United States Patent
Aparin

(10) Patent No.: US 10,488,365 B2
(45) Date of Patent: Nov. 26, 2019

(54) CURRENT SENSORS USING BIPOLAR TRANSISTORS

(71) Applicant: QUALCOMM Incorporated, San Diego, CA (US)

(72) Inventor: Vladimir Aparin, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 459 days.

(21) Appl. No.: 15/181,596

(22) Filed: Jun. 14, 2016

(65) Prior Publication Data

US 2016/0370313 A1    Dec. 22, 2016

Related U.S. Application Data

(60) Provisional application No. 62/181,158, filed on Jun. 17, 2015.

(51) Int. Cl.
| | | |
|---|---|---|
| *G01N 27/327* | (2006.01) | |
| *G01N 27/416* | (2006.01) | |
| *G01N 33/483* | (2006.01) | |
| *G01N 21/27* | (2006.01) | |

(Continued)

(52) U.S. Cl.
CPC ............ *G01N 27/416* (2013.01); *G01N 21/27* (2013.01); *G01N 27/3276* (2013.01); *G01N 27/4145* (2013.01); *G01N 27/4148* (2013.01); *G01N 27/4167* (2013.01); *G01N 33/4836* (2013.01); *G01N 33/48721* (2013.01)

(58) Field of Classification Search
CPC ..... G01N 27/3275–3278; G01N 27/27; G01N 33/4836; G01N 21/27; G01N 21/01
See application file for complete search history.

(56) References Cited

U.S. PATENT DOCUMENTS

| | | | |
|---|---|---|---|
| 4,118,689 A | 10/1978 | Peil et al. | |
| 4,225,410 A * | 9/1980 | Pace | G01N 33/492 |
| | | | 204/406 |
| 5,111,221 A | 5/1992 | Fare et al. | |

(Continued)

FOREIGN PATENT DOCUMENTS

| | | |
|---|---|---|
| CN | 103675073 A | 3/2014 |
| CN | 104105797 A | 10/2014 |

(Continued)

OTHER PUBLICATIONS

Purushothaman et al., "Towards Fast Solid State DNA Sequencing," 2002 IEEE International Symposium on Circuits and Systems Proceedings (Cat. No. 02CH37353) (Year: 2002).*

(Continued)

*Primary Examiner* — Alexander S Noguerola
(74) *Attorney, Agent, or Firm* — Patterson & Sheridan, L.L.P.

(57) ABSTRACT

Certain aspects of the present disclosure provide methods and apparatus for sensing. One example apparatus for sensing includes a sensor configured to supply a current indicative of a parameter and a bipolar transistor having a base coupled to the sensor to receive the current, the bipolar transistor being configured to generate an amplified current based on the current. The apparatus may also include a measurement circuit coupled to the bipolar transistor and configured receive the amplified current.

48 Claims, 10 Drawing Sheets

(51) Int. Cl.
　　*G01N 33/487*　　(2006.01)
　　*G01N 27/414*　　(2006.01)

(56) References Cited

U.S. PATENT DOCUMENTS

| | | | | |
|---|---|---|---|---|
| 5,362,971 | A * | 11/1994 | McMahon | G01N 21/431 250/577 |
| 6,916,614 | B1 * | 7/2005 | Takenaka | G01N 27/3275 204/403.01 |
| 2004/0207384 | A1 | 10/2004 | Brederlow et al. | |
| 2004/0262636 | A1 | 12/2004 | Yang et al. | |
| 2005/0029099 | A1 * | 2/2005 | Eversmann | G01N 27/4145 204/416 |
| 2011/0204455 | A1 | 8/2011 | Kang et al. | |
| 2012/0138460 | A1 | 6/2012 | Baghbani-Parizi et al. | |
| 2012/0312083 | A1 | 12/2012 | Akahori et al. | |
| 2014/0030838 | A1 | 1/2014 | Cai et al. | |

FOREIGN PATENT DOCUMENTS

| | | |
|---|---|---|
| KR | 20120000369 A | 1/2012 |
| WO | WO-2010122293 A1 | 10/2010 |
| WO | WO-2011067559 A1 | 6/2011 |
| WO | WO-2014066909 A1 | 5/2014 |
| WO | 2014204394 A1 | 12/2014 |

OTHER PUBLICATIONS

Lacina et al., "Bipolar transistor amplifier for transduction of electrochemical response to visual perception," Sensors and Actuators B: Chemical 210 (2015) 183-189 (Year: 2015).*
Article entitled "Transistor Darlington Pair Tutorial" downloaded on Nov. 5, 2018 from https://www.radio-electronics.com/info/circuits/transistor/darlington-pair-amplifier.php (Year: 2018).*
EPO computer-generated English translation of CN 103675073 A (Year: 2014).*
Sansen, Willy M.C. "Analog Integrated Circuit Design Essentials", Springer, 2006, pp. 68-74. (Year: 2006).*
Jafari H.M., et al., "Chopper-Stabilized Bidirectional Current Acquisition Circuits for Electrochemical Amperometric Biosensors", IEEE Transactions on Circuits and Systems I: Regular Papers, IEEE, US, vol. 60, No. 5, Apr. 24, 2013 (Apr. 24, 2013), pp. 1149-1157, XP011505601, ISSN: 1549-8328, DOI: 10.1109/TCSI.2013. 2248771 p. 1149, left-hand column, line 16-p. 1156, right-hand column, line 15; figures 5,12.
Anonymous: "Chapter 10: Multi stage Amplifier Configurations [Analog Devices Wiki]", Sep. 21, 2013 (Sep. 21, 2013), XP055297332, Retrieved from the Internet: URL: https://wiki.analog.com/university/courses/electronics/text/chapter-10?rev;1379775557 [retrieved on Aug. 24, 2016] the whole document.
Anonymous: "Chapter 11: The Current Mirror [Analog Devices Wiki]", Jan. 9, 2014 (Jan. 9, 2014), XP055297326, Retrieved from the Internet: https://wiki.analog.com/university/courses/electronics/text/chapter-11 [retrieved on Aug. 24, 2016] the whole document.
Chen., et al., "Extended Base H+-ion Sensitive Bipolar Junction Transistor with Sn02/ITO Glass Sensing Membrane", sensors, 2009 IEEE, IEEE, Piscataway, NJ, USA, Oct. 25, 2009 (Oct. 25, 2009), pp. 1113-1116, XP031618979, ISBN: 978-1-4244-4548-6 p. 1113. right-hand column, paragraph 3-paragraph 5 figures 2,3.
Chen L., et al., "High Gain Current Readout Method for MWCNT Infrared Sensor", 2012 12th IEEE International Conference on Nanotechnology (IEEE-Nano 2012) : Birmingham, United Kingdom, Aug. 20-23, 2012, IEEE, Piscataway, NJ, Aug. 20, 2012 (Aug. 20, 2012), pp. 1-4, XP032260314, DOI: 10.1109/NANO.2012. 6322158 ISBN: 978-1-4673-2198-3 paragraph [II.B.] figure 3.
International Search Report and Written Opinion—PCT/US2016/037544—ISA/EPO—dated Sep. 7, 2016.
Sansen Willy Kc., "Analog Integrated Circuit Design Essentials", Tsinghua University Press, Mar. 2008, 1st Edition, pp. 49-51.

* cited by examiner

US 10,488,365 B2

CURRENT SENSORS USING BIPOLAR TRANSISTORS

CLAIM OF PRIORITY UNDER 35 U.S.C. § 119

The present application claims the benefit of U.S. Provisional Patent Application Ser. No. 62/181,158, entitled "IONIC CURRENT SENSORS USING BIPOLAR TRANSISTORS" and filed Jun. 17, 2015, which is assigned to the assignee of the present application and hereby expressly incorporated by reference herein in its entirety.

TECHNICAL FIELD

Certain aspects of the present disclosure generally relate to electronic circuits and, more particularly, to current sensors using bipolar transistors.

BACKGROUND

A transducer is a device used to convert one form of energy to another form of energy. A sensor is a transducer designed to detect (that is, to sense) a characteristic of the sensors environment in one form and indicate this characteristic in another form, which may be an electric signal. For example, ionic current sensors may be used to convert an ionic current flow of a medium to an electrical signal, such that the electrical signal may be further processed (e.g., amplified, filtered, digitized, etc.).

SUMMARY

Certain aspects of the present disclosure generally relate to current sensors (e.g., ionic current sensors) using bipolar transistors.

Certain aspects of the present disclosure provide an apparatus for sensing. The apparatus generally includes a sensor configured to supply a current indicative of a parameter, a bipolar transistor having a base coupled to the sensor to receive the current, the bipolar transistor being configured to generate an amplified current based on the current, and a measurement circuit coupled to the bipolar transistor and configured receive the amplified current.

Certain aspects of the present disclosure provide a method for sensing. The method generally includes receiving a base current at a base of a bipolar transistor, the base current being indicative of a parameter, amplifying the base current using the bipolar transistor to generate an amplified current, and determining the parameter based on the amplified base current.

Certain aspects of the present disclosure provide an apparatus for sensing. The apparatus generally includes means for receiving a base current at a base of a bipolar transistor, the base current being indicative of a parameter, means for amplifying the base current using the bipolar transistor to generate an amplified current, and means for determining the parameter based on the amplified base current.

Certain aspects of the present disclosure provide a device. The device generally includes a plurality of measurement cells, each measurement cell comprising a sensor configured to supply a current indicative of a parameter, and a bipolar transistor having a base coupled to the sensor to receive the current, the bipolar transistor being configured to generate an amplified current based on the current, and a plurality of analog-to-digital converters, wherein the output of the bipolar transistor from the plurality of measurement cells is selectively coupled to one analog-to-digital converter of the plurality of analog-to-digital converters.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects.

DETAILED DESCRIPTION

Various aspects of the present disclosure are described below. It should be apparent that the teachings herein may be embodied in a wide variety of forms and that any specific structure, function, or both being disclosed herein is merely representative. Based on the teachings herein, one skilled in the art should appreciate that an aspect disclosed herein may be implemented independently of any other aspects and that two or more of these aspects may be combined in various ways. For example, an apparatus may be implemented or a method may be practiced using any number of the aspects set forth herein. In addition, such an apparatus may be implemented or such a method may be practiced using other structure, functionality, or structure and functionality in addition to or other than one or more of the aspects set forth herein. Furthermore, an aspect may comprise at least one element of a claim.

The word "exemplary" is used herein to mean "serving as an example, instance, or illustration." Any aspect described herein as "exemplary" is not necessarily to be construed as preferred or advantageous over other aspects.

Example Current Sensors

Figure 1:
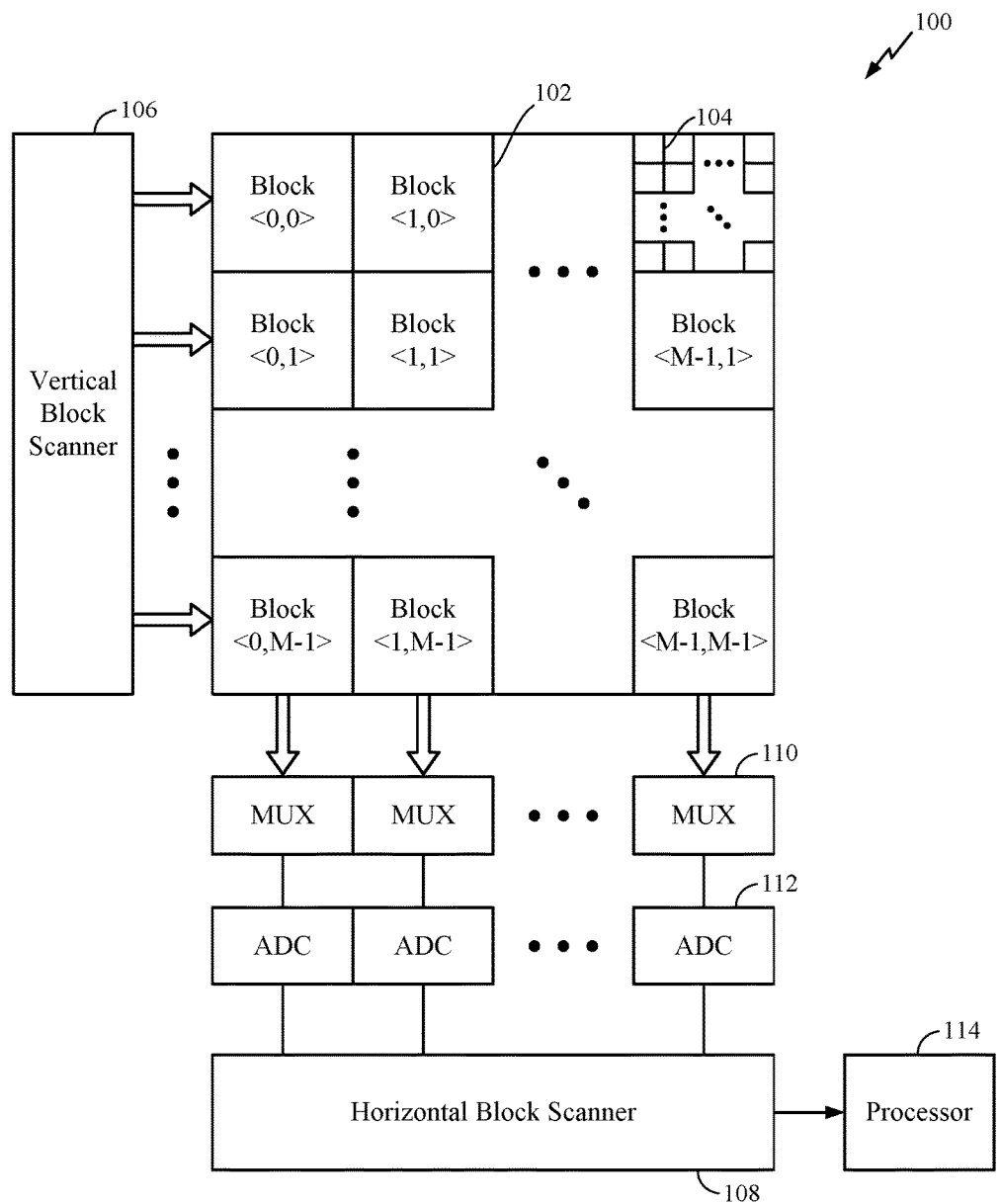
FIG. 1 is an example system having a sensor array and a processing system for controlling scanning of the sensor array.

Certain aspects of the present disclosure provide methods and apparatus for determining a parameter of a medium using a current sensor implemented with a bipolar transistor. The current sensor may be one of a plurality of current sensors in a sensor array configured to convert an ionic current flow of a medium to an electrical signal, FIG. 1 is an example system having a sensor array 100 and a processing system for controlling scanning of the sensor array. As illustrated, the current sensor array 100 includes a plurality of blocks 102, each including a plurality of measurement cells 104. A vertical block scanner 106 may be used to select each measurement cell 104 in a row for current measurement. For example, each measurement cell 104 may include a current sensing circuit (not shown in FIG. 1) that may be activated via a switch by the vertical block scanner 106.

Once a current measurement is made by a measurement cell 104, the current measurement output of the measurement cell 104 may be communicated to a horizontal block scanner 108. For example, the current sensor array 100 may include a plurality of multiplexers 110 (MUXes) that may be used to select an output signal of a respective measurement cell 104. The selected output, which may be in analog form, may be sent to an analog-to-digital converter (ADC) 112 where the analog output is converted to a digital signal. The digital representation of the measured current by a corresponding measurement cell 104 is then sent to the horizontal block scanner 108. The horizontal block scanner 108 may communicate the digital representation of the measured current to a processor 114 for analysis.

Each measurement cell 104 of the current sensor array 100 may be configured to sense (e.g., measure) a current flow across a medium. The measurement of the current flow may be indicative of a property associated with the medium through which the current is flowing, as described in more detail herein.

Figure 2:
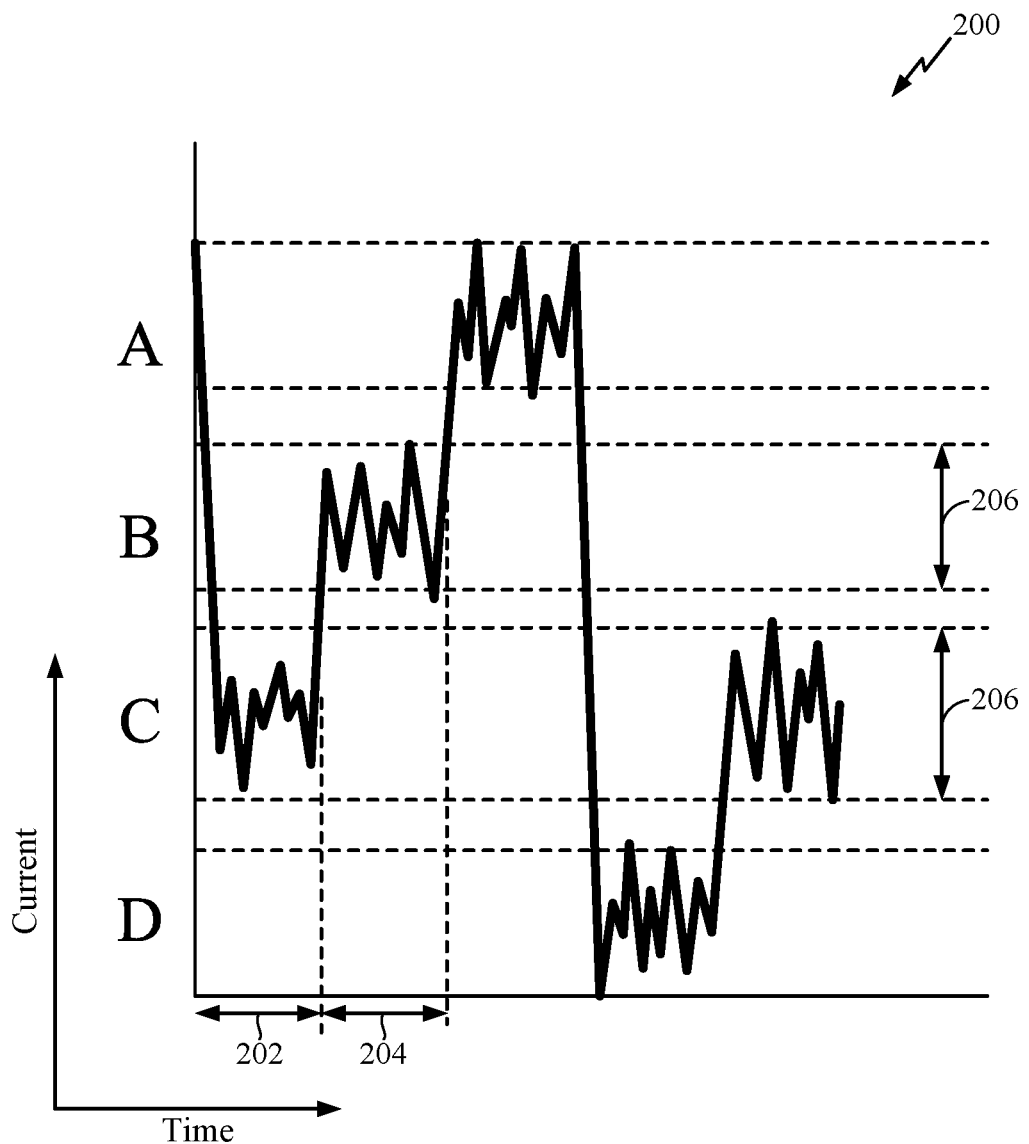
FIG. 2 is an example graph showing change in current flow in a medium as a function of a property of the medium.

FIG. 2 is a graph 200 illustrating example levels of current flow in a medium as a function of a property associated with the medium. That is, a current measurement having a specific average, which may be measured across a period 202, that is within a specific range may indicate a property associated with the medium. For example, a current measurement during period 202 may be indicative of property C, and a current measurement during period 204 may be indicative of property B, as illustrated.

An amount of noise may be coupled onto the current measurements of each measurement cell 104. For example, the noise of the current measurements may have a noise amplitude 206. If the noise amplitude of the current measurements is too large, it may become increasingly difficult to distinguish between one property of the medium and another. That is, it may become difficult to determine a property of the medium that a current measurement represents, resulting in errors. For example, if the current measurement noise flowing through a medium having property C is too large, the current measurement may be mistakenly associated with property B. Aspects of the present disclosure provide apparatus and techniques for reducing the current measurement noise.

Figure 3:
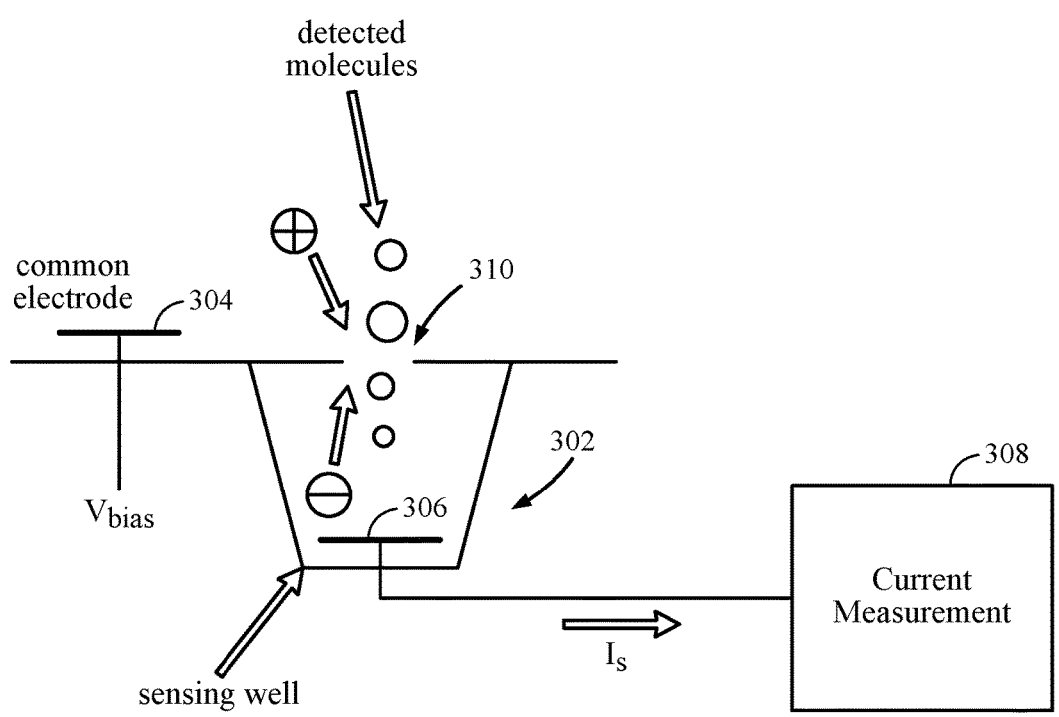
FIG. 3 illustrates an example sensing well used to detect molecules in a medium.

FIG. 3 illustrates an example sensing well 302 used to detect molecules in a medium. For example, each of the measurement cells 104 of the current sensor array 100 may include a sensing well 302 for detecting molecules. Each sensing well may be covered with a membrane and a nanopore 310 (e.g., opening) per sensing well. The sensing well 302 and the space above the sensing well may contain an ionic solution. Two electrodes may be used to generate current flow (e.g., sensing current (Is)) in the ionic solution. For example, a bias voltage (Vbias) may be applied to an electrode 304, which may be a common electrode across all, or a portion, of sensing wells of the current sensor array 100. In certain aspects, Vbias may be supplied via a voltage supply (not shown). By applying Vbias to the electrode 304, sensing current Is may flow from the electrode 304, through the medium (e.g., through the nanopore) and to an electrode 306 (e.g., a sensing mechanism). From the electrode, the sensing current Is may flow into a current measurement circuit 308, where the sensing current Is may be amplified and measured.

Variations in the level of sensing current Is flow measured by the current measurement may indicate a property associated with the medium, as described above with respect to FIG. 2. For example, different levels of current flow may indicate different molecules that are present in the sensing well. That is, molecules that are to be detected can be positively charged identification tags of deoxyribonucleic acid (DNA) bases, freed up during polymerase reaction above the nanopore. These tags move away from the electrode 304 towards the electrode 306. When a tag moves through the nanopore, it blocks the ionic current through the nanopore, thus changing the level of current flow (e.g., sensing current Is) into the current measurement circuit 308 in a manner that is dependent on the size of the tag.

As presented above with respect to FIG. 2, if the current measurement noise flowing through the medium (e.g., the ionic solution in sensing well 302) is too large, it may be difficult to detect the property of the medium. For example, a type of nucleobase in a DNA fragment in the ionic solution of the sensing well 302 may be detected in error (e.g., misidentified). The current measurement noise may be caused by the current measurement circuit 308. Thus, aspects of the present disclosure provide apparatus and techniques for reducing the current measurement noise of the current measurement circuit 308. For example, a bipolar transistor having low noise (e.g., as opposed to a field-effect transistor (FET)) may be used to amplify and measure the current Is.

Figure 4A:
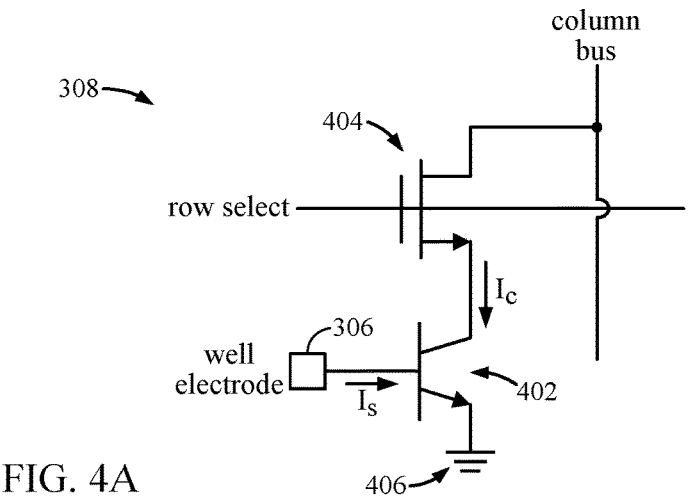
FIGS. 4A-4F illustrate example current measurement circuits using a n-doped/p-doped/n-doped (npn) bipolar transistor for current amplification, in accordance with certain aspects of the present disclosure.

FIG. 4A is an example current measurement circuit 308 using a bipolar transistor 402 for current amplification, in accordance with certain aspects of the present disclosure. As illustrated, the sensing current Is may flow into a base of the bipolar transistor 402. A collector of the bipolar transistor 402 may be coupled to an activation switch 404, which may be implemented using a FET. The activation switch 404 may be activated (e.g., closed) using a row select signal that may be controlled by the vertical block scanner 106 to activate the current sensing circuit 308. Once activated, the base current of the bipolar transistor 402 (i.e., sensing current Is) may be amplified with a current gain beta ($\beta$) (e.g., corresponding to bipolar transistor 402) such that the collector current Ic is about equal to $\beta \times$Is. That is, the collector current Ic flows from the column bus to a reference potential 406 (e.g., electrical ground), and is measured and digitized by a corresponding ADC 112, and communicated to the horizontal block scanner 108 of FIG. 1.

Figure 4B:
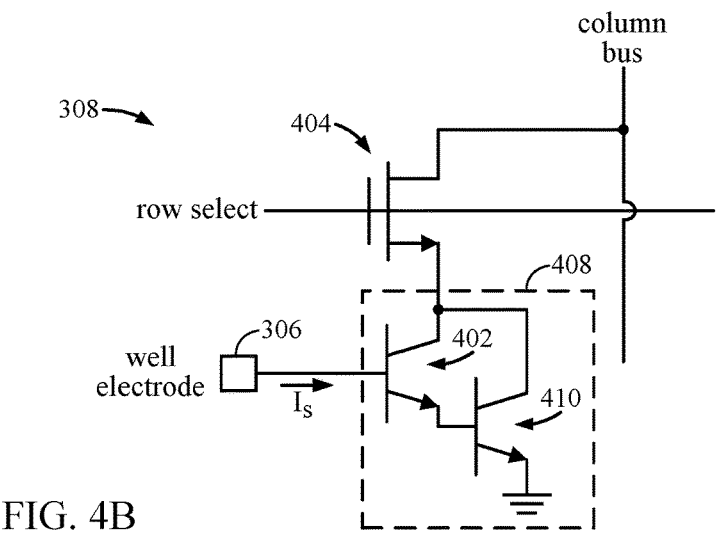

FIG. 4B is an example current measurement circuit 308 using a Darlington pair configuration of bipolar transistors 408 for current amplification, in accordance with certain aspects of the present disclosure. As illustrated, the emitter of the bipolar transistor 402 may be coupled to a base of another bipolar transistor 410 such that the collector current of the bipolar transistor 402 is further amplified by bipolar transistor 410. Thus, the Darlington pair configuration of bipolar transistors 408 provides a higher gain as compared to using a single bipolar transistor for amplification of the sensing current Is.

Figure 4C:
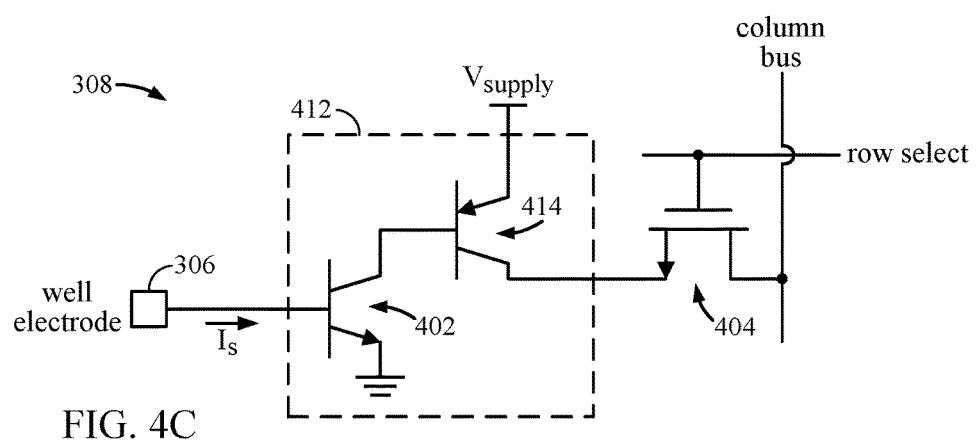

FIG. 4C is an example current measurement circuit 308 using a Sziklai pair configuration of bipolar transistors 412 for current amplification, in accordance with certain aspects of the present disclosure. As illustrated, the collector of the bipolar transistor 402 (e.g., an n-doped/p-doped/n-doped (npn) transistor) is coupled to a base of a p-doped/n-doped/p-doped (pnp) bipolar transistor 414. The emitter of the bipolar transistor 414 is coupled to a supply voltage, from which an amplified current flows to the column bus based on the collector current of bipolar transistor 402. Thus, the bipolar transistor 414 increases the amplification gain of sensing current Is. An activation switch 404, which may be implemented as a FET, is connected between the collector of bipolar transistor 414 and the column bus, and used to activate the current measurement circuit 308 of FIG. 4C.

Figure 4D:
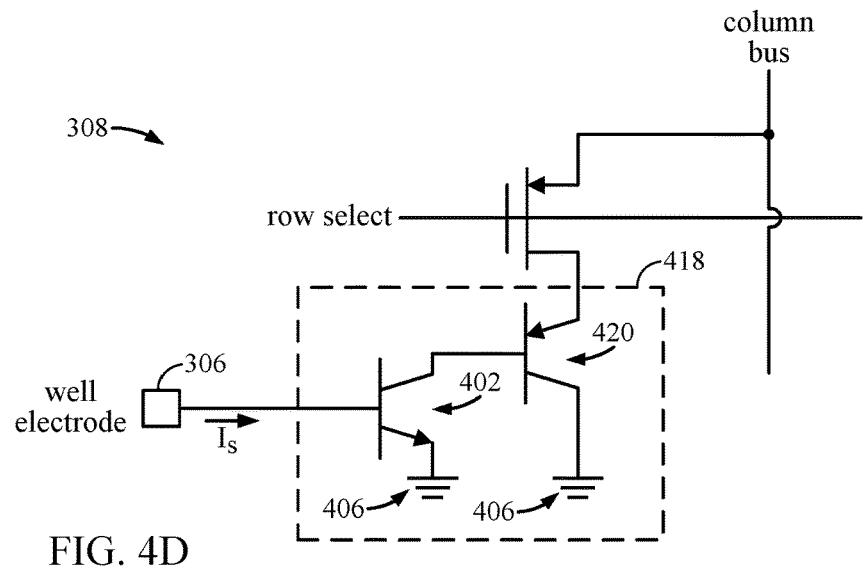

FIG. 4D is an example current measurement circuit 308 using npn and pnp bipolar transistors 418 for current amplification, in accordance with certain aspects of the present disclosure. As illustrated, the collector of bipolar transistor 402 (e.g., an npn bipolar transistor) may be coupled to a base of a pnp bipolar transistor 420, which further amplifies the collector current of bipolar transistor 402. The emitter of bipolar transistor 402 and collector of bipolar transistor 420 are coupled to a reference potential 406. The emitter current of bipolar transistor 420 may flow from the column bus when the activation switch 404 is closed, and a digital representation of the emitter current of bipolar transistor 420 is sent to the horizontal block scanner 108 via a corresponding ADC 112.

The bipolar transistor 402 in each of FIGS. 4A-4D has a base connected to the electrode 306 and an emitter connected to a reference potential 406 (e.g., either directly, or through a base-emitter connection of another transistor). Thus, the bipolar transistor 402 of FIGS. 4A-4D can establish a current-insensitive voltage at the electrode 306, without using an operational-amplifier (op-amp) to generate such a voltage, because the base-emitter voltage (Vbe) of a bipolar transistor is a logarithmic function of the base current (e.g., Is). By using a bipolar transistor as opposed to an op-amp to establish a current-insensitive voltage at the electrode 306, the area occupied by the current measurement circuit 308 is reduced, allowing for a higher degree of integration. Moreover, bipolar transistors provide local amplification of the sensing current Is, thus reducing the noise contributions from leakage paths and readout circuits. Bipolar transistors also reduce current measurement noise as compared to FETs as bipolar transistors may have one to two orders of magnitude lower noise than FETs.

Figure 4E:
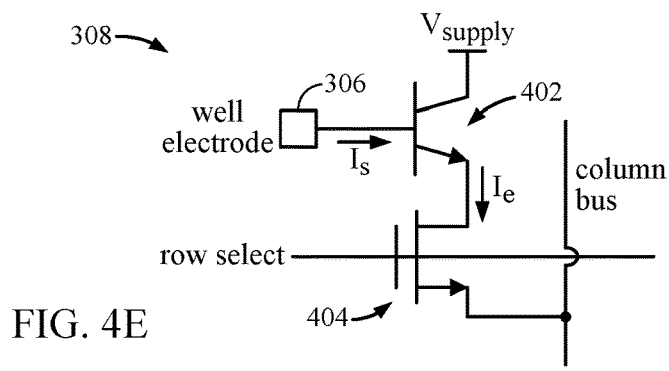

FIG. 4E is an example current measurement circuit 308 using a bipolar transistor 402 for current amplification having a collector coupled to a supply voltage, in accordance with certain aspects of the present disclosure. As illustrated, the bipolar transistor 402 of FIG. 4E amplifies the sensing current Is and provides an emitter current Ie from a supply voltage (Vsupply) to the column bus when the activation switch 404 is closed.

Figure 4F:
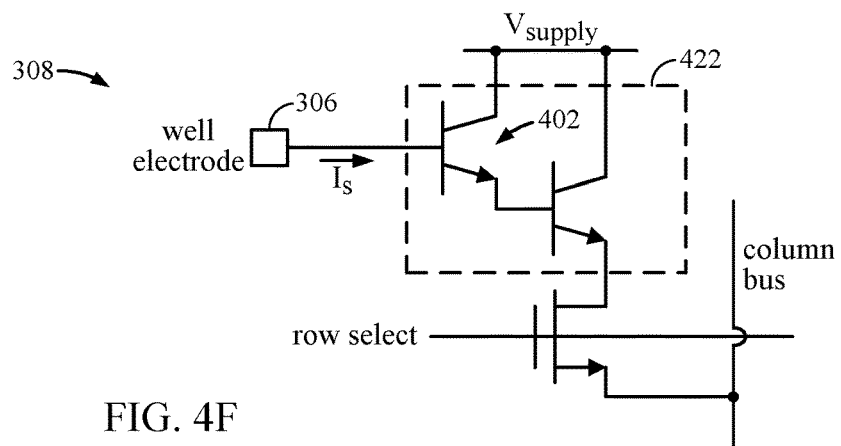

FIG. 4F is an example current measurement circuit 308 using a Darlington pair configuration of bipolar transistors 422 for current amplification having collectors coupled to a supply voltage (Vsupply), in accordance with certain aspects of the present disclosure. As presented above with respect to FIG. 4B, the Darlington pair configuration of transistors provides a higher current amplification gain as compared to using a single bipolar transistor for current amplification.

Figure 5A:
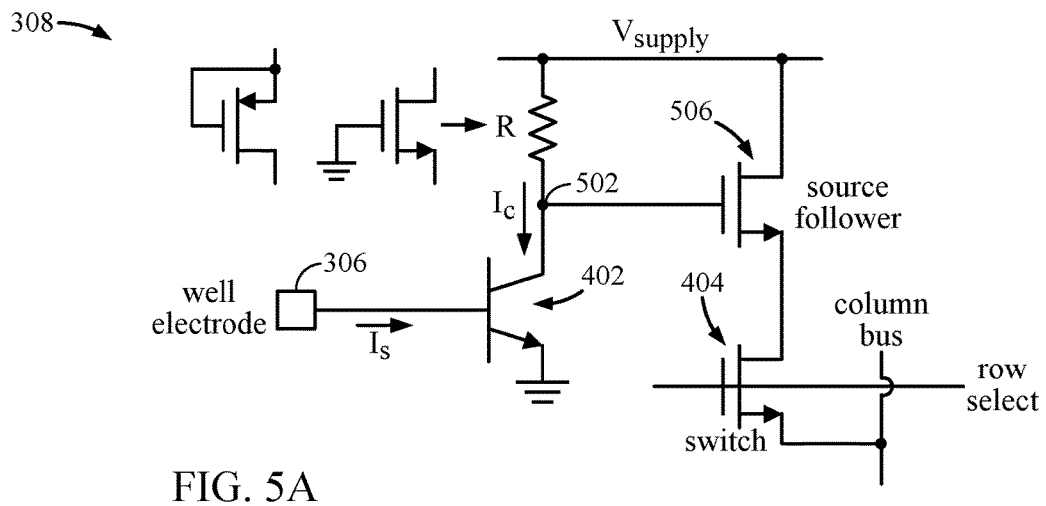
FIGS. 5A and 5B illustrate example current measurement circuits configured to amplify, via an npn transistor, and convert a sensing current to a voltage, in accordance with certain aspects of the present disclosure.

FIG. 5A is an example current measurement circuit 308 configured to amplify, via a bipolar transistor 402, and convert the current Is to a voltage via a resistive element R, in accordance with certain aspects of the present disclosure. That is, the collector current Ic flows through the resistive element R coupled to a supply voltage (Vsupply). Thus, a voltage at node 502 may be equal to the supply voltage, less a voltage drop across the resistive element R, which is a function of the collector current Ic. Thus, the current Ic effectively controls a gate voltage of a source follower 506 (e.g., a buffer), which may be in a triode region. The voltage at the column bus may be equal to the supply voltage, less the drain-to-source voltage drop across the source follower 506, when an activation switch 404 is closed. Thus, the voltage at the column bus may be representative of the voltage at node 502, which is controlled by the bipolar transistor 402 based on the sensing current Is. As illustrated, the resistive element R may be implemented in various ways, such as using a polysilicon resistor, an ion-impact resistor, or a FET (e.g., a n-type FET (NFET) biased in a triode region or a turned off NFET or p-type FET (PFET).

Figure 5B:
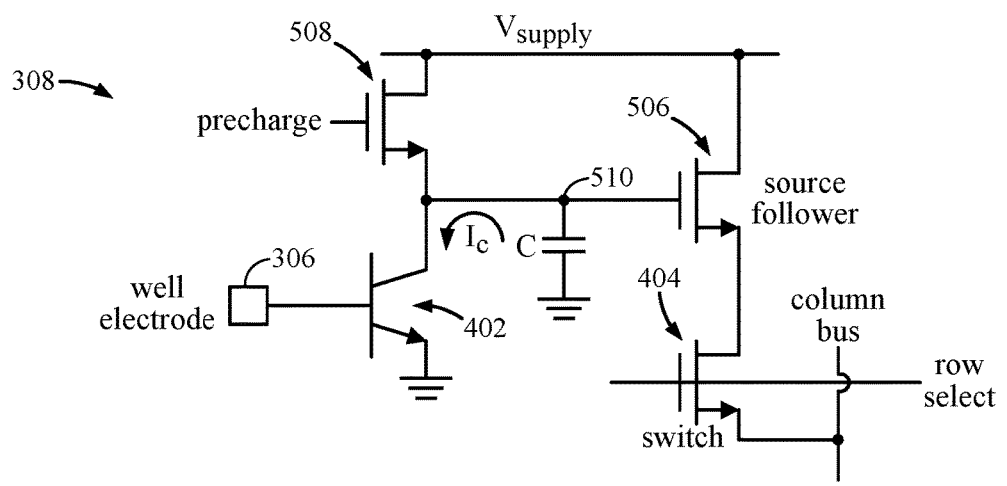

FIG. 5B is an example current measurement circuit 308 configured to convert the sensing current Is to a voltage via a shunt capacitor C, in accordance with certain aspects of the present disclosure. That is, the shunt capacitor C may be coupled to a node 510 between a collector of the bipolar transistor 402 and a precharge switch 508. The precharge switch 508 may be configured to, when closed, charge the shunt capacitor C to a supply voltage level. Once the shunt capacitor C is precharged, the precharge switch may be opened. Thus, the collector current Ic of the bipolar transistor 402 may flow from and discharge the shunt capacitor C, in effect, integrating the collector current Ic via the shunt capacitor C. By discharging the shunt capacitor C, the voltage across the shunt capacitor C is reduced. The voltage across shunt capacitor C also depends on an amount of time the capacitor is discharged, which is configured to be the same for all sensing wells of the plurality of measurement cells 104. By adjusting the voltage across shunt capacitor C, a voltage at the gate of a source follower 506 is adjusted. As presented above with respect to FIG. 5A, by adjusting the voltage at the gate of the source follower 506, a voltage at the column bus may be adjusted when the activation switch 404 is closed.

In some cases, the current flow through the medium may flow away from the current measurement circuit 308. That is, the electrode 304 may be at a lower voltage potential than the electrode 306 such that current flows through the sensing well 302 from the electrode 306 to the electrode 304. Therefore, certain aspects of the present disclosure are directed to current measurement circuits that can measure the sensing current flowing away from the current measurement circuit 308.

Figure 6A:
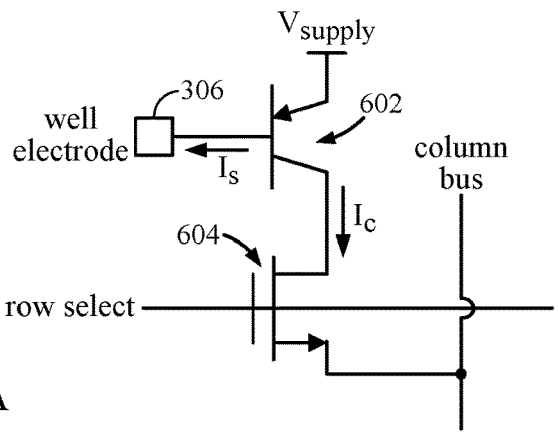
FIGS. 6A-6F illustrate example current measurement circuits using a p-doped/n-doped/p-doped (pnp) bipolar transistor for current amplification, in accordance with certain aspects of the present disclosure.

FIG. 6A is an example current measurement circuit 308 using a pnp bipolar transistor 602 for current amplification, in accordance with certain aspects of the present disclosure. As illustrated, the sensing current Is may flow away from a base of the bipolar transistor 602. A collector of the bipolar transistor 602 may be coupled to an activation switch 604, which may be implemented using a FET. The activation switch 604 may be activated (e.g., closed) using a row select signal that may be controlled by the vertical block scanner 106 to activate the current sensing circuit 308. Once activated, the base current of the bipolar transistor 602 (e.g., sensing current Is) may be amplified with a current gain beta ($\beta$) such that the collector current Ic is about equal to $\beta \times Is$. That is, the collector current Ic flows from the supply voltage at the emitter of bipolar transistor 602, and towards the column bus, is measured and digitized by a corresponding ADC 112, and communicated to the horizontal block scanner 108.

Figure 6B:
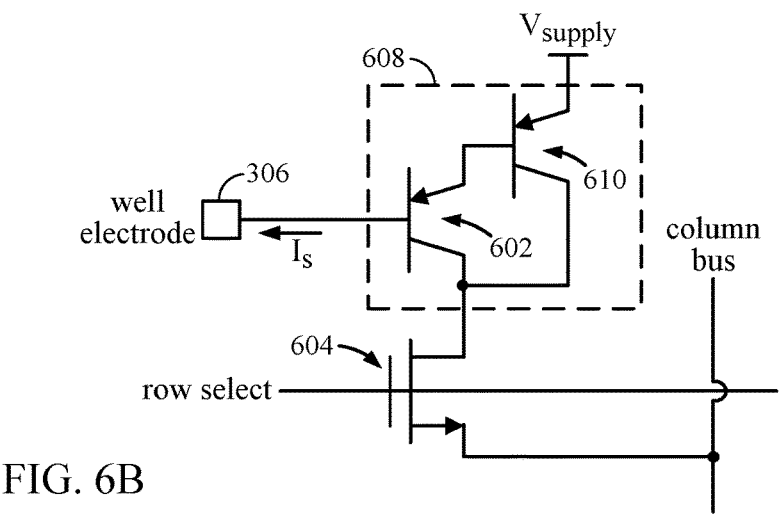

FIG. 6B is an example current measurement circuit 308 using a Darlington pair configuration of pnp bipolar transistors 608 for current amplification, in accordance with certain aspects of the present disclosure. As illustrated, the emitter of bipolar transistor 602 may be coupled to a base of another bipolar transistor 610 such that the emitter current of bipolar transistor 602 is further amplified by bipolar transistor 610. Thus, the Darlington pair configuration of bipolar transistors 608 provides a higher gain as compared to using a single bipolar transistor for amplification of the sensing current Is.

Figure 6C:
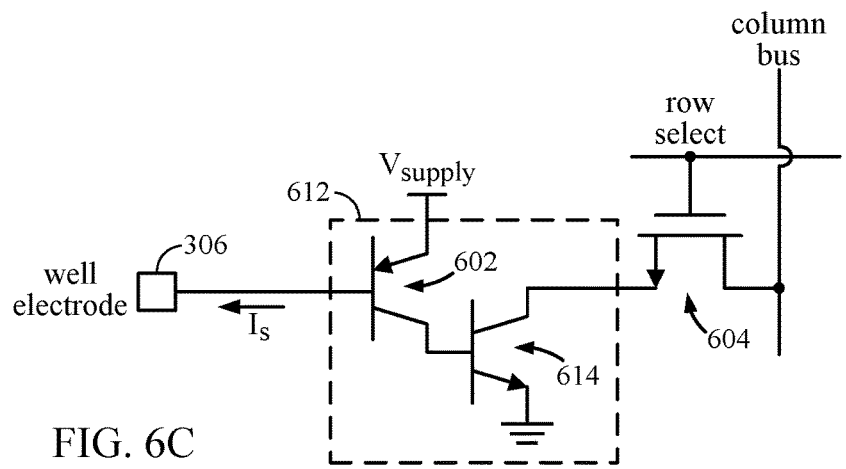

FIG. 6C is an example current measurement circuit 308 using a Sziklai pair configuration of bipolar transistors 612 for current amplification, in accordance with certain aspects of the present disclosure. As illustrated, the collector of the pnp bipolar transistor 602 is coupled to a base of a npn transistor 614 and the emitter of bipolar transistor 614 is coupled to a reference potential. The bipolar transistor 614 amplifies the collector current of the bipolar transistor 602, and increases the amplification gain of sensing current Is. An activation switch 604, which may be implemented as a FET, may be connected between the collector of the bipolar transistor 614 and the column bus, and used to activate the current measurement circuit 308 of FIG. 6C.

Figure 6D:
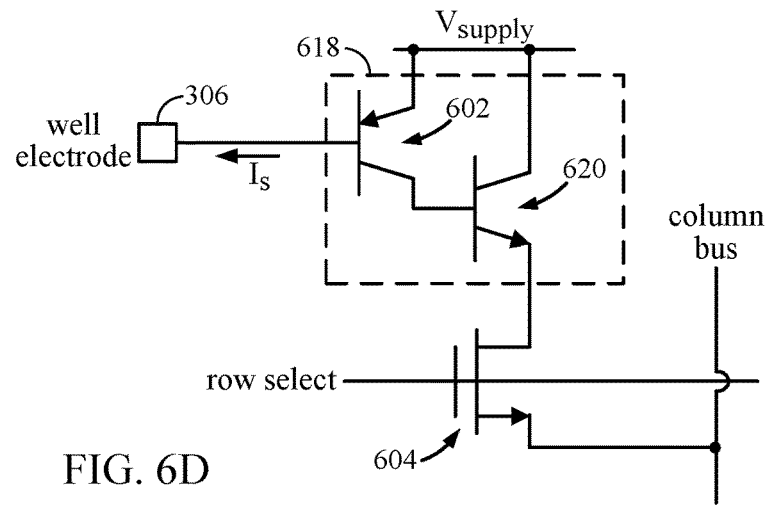

FIG. 6D is an example current measurement circuit 308 using pnp and npn bipolar transistors 618 for current amplification, in accordance with certain aspects of the present disclosure. As illustrated, the collector of bipolar transistor 602 (e.g., a pnp transistor) may be coupled to a base of a npn transistor 620, which further amplifies the collector current of bipolar transistor 602. The emitter of bipolar transistor 602 and collector of the bipolar transistor 620 are coupled to a supply voltage (Vsupply). The emitter current of the bipolar transistor 620 may flow from the supply voltage to the column bus when the activation switch 604 is closed, and a digital representation of the emitter current of the bipolar transistor 620 is sent to the horizontal block scanner via a corresponding ADC 112.

The bipolar transistor 602 in each of FIGS. 6A-6D has a base connected to the electrode 306 and an emitter connected to a supply voltage (e.g., either directly, or through an emitter-base connection of another transistor). Thus, the bipolar transistor 602 of FIGS. 6A-6D can establish a current-insensitive voltage at the electrode 306, without using an operational-amplifier (op-amp) to generate such a voltage. That is because the emitter-base voltage (Veb) of a bipolar transistor is a logarithmic function of the base current (e.g., Is). By using a bipolar transistor as opposed to an op-amp to establish a current-insensitive voltage at the electrode 306, the area occupied by the current measurement circuit 308 is reduced, allowing for a higher degree of integration. Moreover, bipolar transistors provide local amplification of the sensing current Is, thus reducing the noise contributions from leakage paths and readout circuits. Bipolar transistors also reduce current measurement noise as compared to FETs as bipolar transistors have one to two orders of magnitude lower noise than FETs.

Figure 6E:
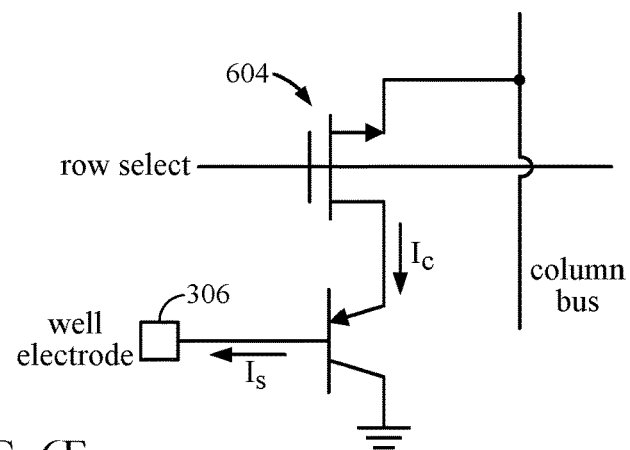

FIG. 6E is an example current measurement circuit 308 using a pnp bipolar transistor 602 for current amplification having a collector coupled to a reference potential, in accordance with certain aspects of the present disclosure. As illustrated, the bipolar transistor 602 of FIG. 6E amplifies the sensing current Is, generating current flow Ie from the column bus to the reference potential when the activation switch 404 is closed.

Figure 6F:
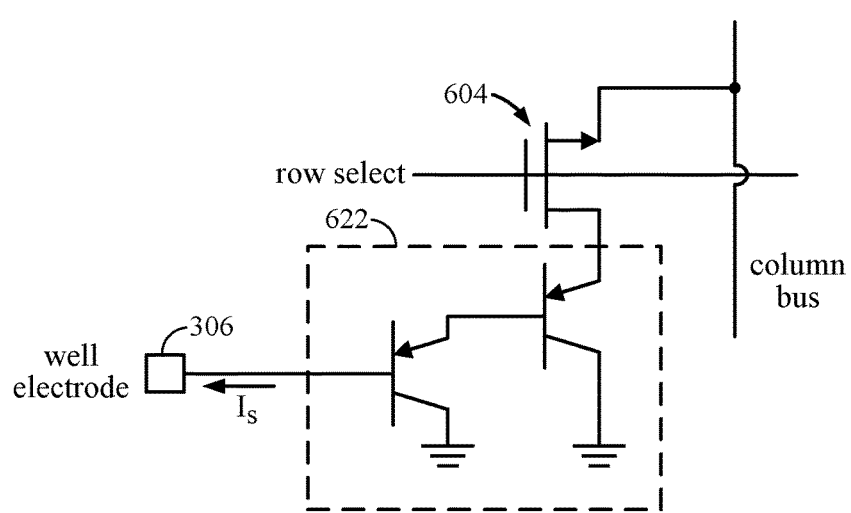

FIG. 6F is an example current measurement circuit 308 using a Darlington pair configuration of pnp bipolar transistors 622 for current amplification having collectors coupled to a reference potential, in accordance with certain aspects of the present disclosure. As presented above with respect to FIG. 6B, the Darlington pair configuration of transistors 622 provides a higher current amplification gain as compared to using a single bipolar transistor for current amplification.

Figure 7A:
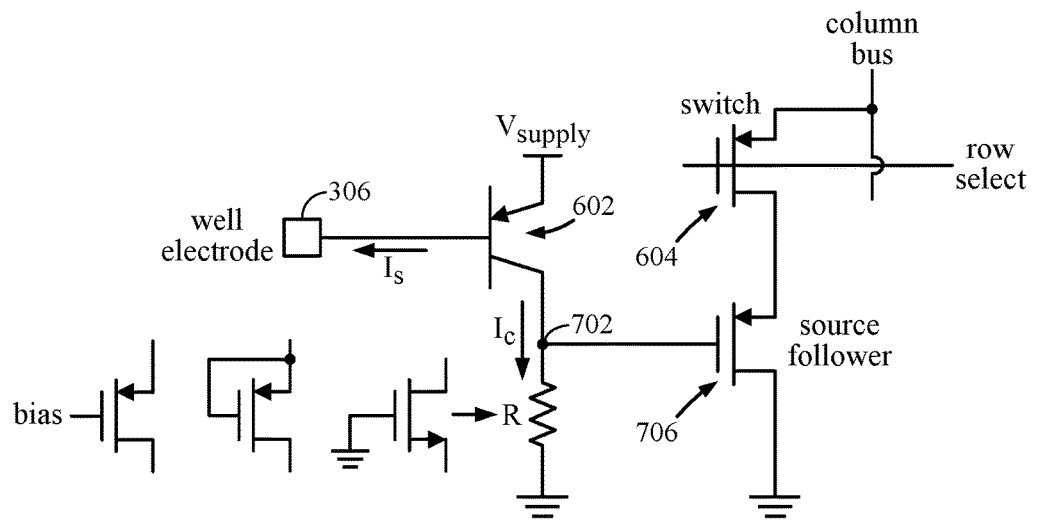
FIGS. 7A and 7B illustrate example current measurement circuits configured to amplify, via a pnp transistor, and convert a sensing current to a voltage, in accordance with certain aspects of the present disclosure.

FIG. 7A is an example current measurement circuit 308 configured to amplify, via a pnp bipolar transistor 602, and convert the sensing current Is to a voltage via a resistive element R, in accordance with certain aspects of the present disclosure. That is, the collector current Ic flows through the resistive element R coupled to a reference potential. Thus, a voltage at node 702 may be equal to a voltage drop across the resistive element R, which is a function of the collector current Ic, less the reference potential. Thus, the current Ic controls a gate voltage of a source follower 706 that may be in a triode region, which in turn adjusts an on-resistance of the source follower 706. The voltage at the column bus is also adjusted by adjusting the on-resistance of the source follower 706, when the activation switch 604 is closed. Thus, the voltage at the column bus may be representative of the voltage at node 702, which is controlled by the bipolar transistor 602 based on the current Is. As illustrated, the resistive element R may be implemented using a FET in various configurations.

Figure 7B:
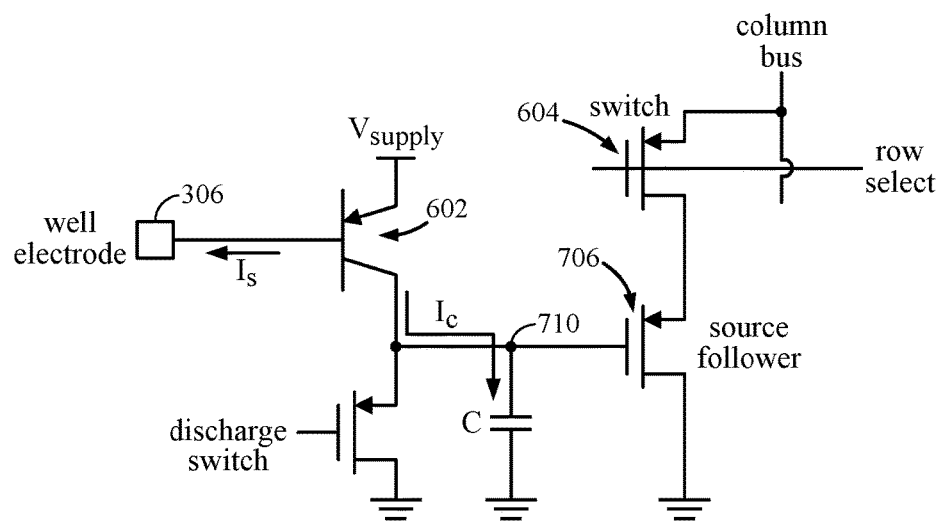

FIG. 7B is an example current measurement circuit 308 configured to amplify, via a pnp bipolar transistor, and convert the sensing current Is to a voltage via a shunt capacitor C, in accordance with certain aspects of the present disclosure. That is, the shunt capacitor C may be coupled to a node 710 between a collector of the bipolar transistor 602 and a discharge switch 708. The discharge switch 708 may be configured to, when closed, discharge the shunt capacitor C. Once the shunt capacitor C is discharged, the discharge switch 708 may be opened. Thus, the collector current Ic of the bipolar transistor 602 may flow to and charge the shunt capacitor C. By charging the shunt capacitor C, the voltage across the shunt capacitor C is increased, adjusting a voltage at the gate of a source follower 706. As presented above with respect to FIG. 5A, by adjusting the voltage at the gate of the source follower 706, a voltage at the column bus may be adjusted when the activation switch 604 is closed.

In certain aspects, the bipolar transistor 402 and/or 602 may be a bipolar junction transistor (BJT) or a heterojunction bipolar transistor (HBT). In some cases, the HBT may be a silicon-germanium (SiGe) HBT. In certain aspects, the discharge switches 508 and 708 may be a PFET or NFET.

Figure 8:
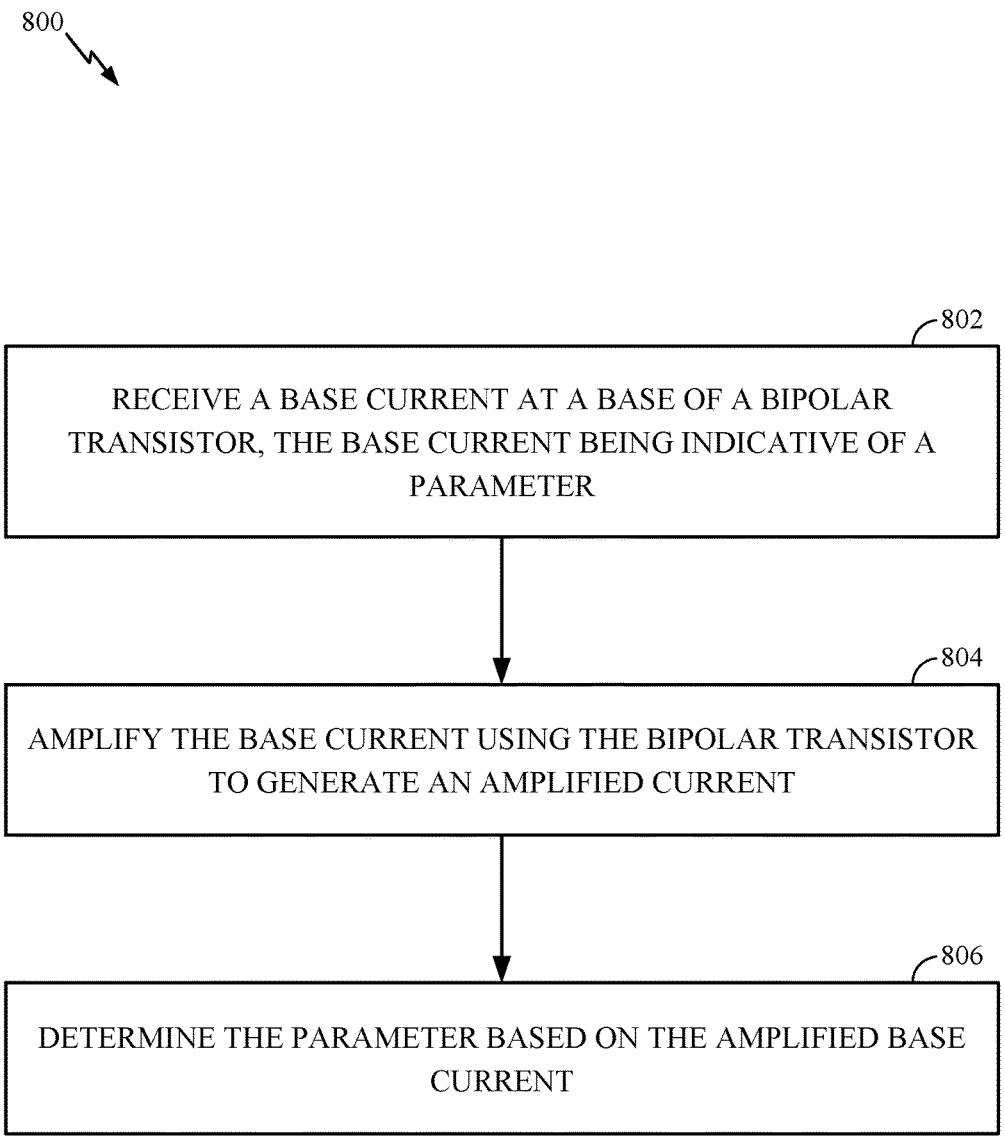
FIG. 8 is a flow diagram of example operations for determining a parameter of a medium, in accordance with certain aspects of the present disclosure.

FIG. 8 is a flow diagram of example operations 800 for determining a parameter of a medium, in accordance with certain aspects of the present disclosure. The operations 800 may be performed by, for example, a device such as the sensor array 100 of FIG. 1 and current measurement circuit 308.

The operations 800 may begin, at block 802, by receiving a base current at a base of a bipolar transistor, the base current being indicative of a parameter. At block 804, the base current may be amplified using the bipolar transistor to generate an amplified current. At block 806, the parameter is determined based on the amplified current.

In some cases, the operations 800 include supplying, by a sensor, the base current to the base of the bipolar transistor.

In this case, the supplying may include generating the base current responsive to one or more photons. For example, the current measured by the current measurement circuit 308 may be based on a detection of light by a photo-diode.

In certain aspects, the supplying includes generating the base current responsive to a current flowing through a medium. The current flowing through the medium may be ionic current. In some cases, the supplying comprises generating the base current based on a pH of the medium, wherein the parameter is the pH of the medium. For example, as the pH of the medium changes, the current flow through the medium may change, as well, and this change in the current flow may be measured to determine the pH of the medium. For example, the current measurement circuit 308 may amplify the current through the medium, and the amplified current can be used to determine the pH of the medium.

In certain aspects, the medium comprises a solution with at least one deoxyribonucleic acid (DNA) fragment and wherein the parameter comprises a type of nucleobase in the DNA fragment. In certain aspects, the medium comprises an electrolytic solution and the determining at block 806 comprises using the amplified base current to detect molecules in the electrolytic solution.

In some cases, the operations 800 also include causing the base current to flow through the medium between a first electrode and a second electrode. In this case, the operations 800 may also include biasing the second electrode with the bipolar transistor. In certain aspects, the operations 800 include biasing the first electrode with a bias voltage.

In certain aspects, the operations 800 further include converting the amplified base current to a sensing voltage, and the determining at block 806 comprises determining the parameter based on the sensing voltage. In certain aspects, the operations 800 may further include buffering the sensing voltage, and the determining at block 806 comprises determining the parameter based on the buffered sensing voltage. In certain aspects, the converting involves passing the amplified current through a resistive element electrically coupled to the bipolar transistor to generate the sensing voltage. In certain aspects, the resistive element comprises at least one of a polysilicon resistor, an ion-implant resistor, a transistor operated in a triode region, or a turned-off transistor.

In certain aspects, the converting entails discharging, to a reference potential during a first period, a capacitor electrically coupled to a collector of the bipolar transistor and allowing a collector current of the bipolar transistor to charge the capacitor during a second period. In certain aspects, the converting involves charging, to a voltage level during a first period, a capacitor electrically coupled to a collector of the bipolar transistor, and allowing a collector current of the bipolar transistor to discharge the capacitor during a second period.

In certain aspects, the amplifying at block 804 entails using another bipolar transistor electrically coupled with the bipolar transistor and configured to increase the overall current amplification of the base current. In certain aspects, the bipolar transistor comprises a bipolar junction transistor (BJT). In other aspects, the bipolar transistor comprises a heterojunction bipolar transistor (HBT). In certain aspects, the HBT comprises a silicon-germanium (SiGe) HBT.

The various operations or methods described above may be performed by any suitable means capable of performing the corresponding functions. The means may include various hardware and/or software component(s) and/or module(s), including, but not limited to a circuit, an application-specific integrated circuit (ASIC), or processor. Generally, where there are operations illustrated in figures, those operations may have corresponding counterpart means-plus-function components with similar numbering. For example, means for causing a current to flow may include a voltage supply to create a voltage difference (e.g., a bias voltage). Means for receiving and/or means for amplifying may include a bipolar transistor, such as the bipolar transistor 402 of FIGS. 4 and 5 or the bipolar transistor 602 of FIGS. 6 and 7. Means for determining may include a processing system including at least one processor, such as the processor 114 of FIG. 1.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, a phrase referring to "at least one of" a list of items refers to any combination of those items, including single members. As an example, "at least one of: a, b, or c" is intended to cover: a, b, c, a-b, a-c, b-c, a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

The various illustrative logical blocks, modules and circuits described in connection with the present invention may be implemented or performed with a general purpose processor, a digital signal processor (DSP), an ASIC, a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware, or any combination thereof. If implemented in hardware, an example hardware configuration may comprise a processing system in a wireless node. The processing system may be implemented with a bus architecture. The bus may include any number of interconnecting buses and bridges depending on the specific application of the processing system and the overall design constraints. The bus may link together various circuits including a processor, machine-readable media, and a bus interface. The bus interface may be used to connect a network adapter, among other things, to the processing system via the bus. The network adapter may be used to implement the signal processing functions of the physical (PHY) layer. In the case of a user terminal, a user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further.

The processing system may be configured as a general-purpose processing system with one or more microprocessors providing the processor functionality and external memory providing at least a portion of the machine-readable media, all linked together with other supporting circuitry through an external bus architecture. Alternatively, the processing system may be implemented with an ASIC with the processor, the bus interface, the user interface in the case of an access terminal), supporting circuitry, and at least a portion of the machine-readable media integrated into a single chip, or with one or more FPGAs, PLDs (Programmable Logic Devices), controllers, state machines, gated logic, discrete hardware components, or any other suitable circuitry, or any combination of circuits that can perform the various functionality described throughout this disclosure. Those skilled in the art will recognize how best to implement the described functionality for the processing system depending on the particular application and the overall design constraints imposed on the overall system.

It is to be understood that the claims are not limited to the precise configuration and components illustrated above. Various modifications, changes and variations may be made in the arrangement, operation and details of the methods and apparatus described above without departing from the scope of the claims.

What is claimed is:

1. A method for sensing, comprising:
    receiving a base current at a base of a bipolar transistor, the base current being indicative of a parameter;
    amplifying the base current using the bipolar transistor to generate an amplified current;
    determining the parameter based on the amplified base current; and
    converting the amplified base current to a sensing voltage, wherein the determining comprises determining the parameter based on the sensing voltage.

2. The method of claim 1, further comprising supplying, by a sensor, the base current to the base of the bipolar transistor.

3. The method of claim 2, wherein the supplying comprises generating the base current responsive to one or more photons.

4. The method of claim 2, wherein the supplying comprises generating the base current responsive to current flowing through a medium.

5. The method of claim 4, wherein the current flowing through the medium comprises ionic current.

6. The method of claim 4, wherein the supplying comprises generating the base current responsive to a pH of the medium and wherein the parameter comprises the pH of the medium.

7. The method of claim 4, wherein the medium comprises a solution with at least one deoxyribonucleic acid (DNA) fragment and wherein the parameter comprises a type of nucleobase in the DNA fragment.

8. The method of claim 4, wherein the medium comprises an electrolytic solution and wherein the determining comprises using the amplified base current to detect molecules in the electrolytic solution.

9. The method of claim 1, further comprising buffering the sensing voltage, wherein the determining comprises determining the parameter based on the buffered sensing voltage.

10. The method of claim 1, wherein the converting comprises passing the amplified current through a resistive element electrically coupled to the bipolar transistor to generate the sensing voltage.

11. The method of claim 10, wherein the resistive element comprises at least one of a polysilicon resistor, an ion-implant resistor, a transistor operated in a triode region, or a turned-off transistor.

12. The method of claim 1, wherein the converting comprises:
    discharging, to a reference potential during a first period, a capacitor electrically coupled to a collector of the bipolar transistor; and
    allowing a collector current of the bipolar transistor to charge the capacitor during a second period.

13. The method of claim 1, wherein the converting comprises:
    charging, to a voltage level during a first period, a capacitor electrically coupled to a collector of the bipolar transistor; and
    allowing a collector current of the bipolar transistor to discharge the capacitor during a second period.

14. The method of claim 1, wherein the amplifying comprises using another bipolar transistor electrically coupled with the bipolar transistor and configured to increase overall current amplification of the base current.

15. A method for sensing, comprising:
    supplying, by a sensor, a base current to a base of a bipolar transistor, wherein the supplying comprises generating the base current responsive to current flowing through a medium;
    receiving the base current at the base of the bipolar transistor, the base current being indicative of a parameter;
    amplifying the base current using the bipolar transistor to generate an amplified current;
    determining the parameter based on the amplified base current;
    causing the base current to flow through the medium between a first electrode and a second electrode; and
    biasing the second electrode with a base-to-emitter voltage ($V_{BE}$) of the bipolar transistor.

16. An apparatus for sensing, comprising:
    a sensor configured to supply a current indicative of a parameter;
    a bipolar transistor having a base coupled to the sensor to receive the current, the bipolar transistor being configured to generate an amplified current based on the current, wherein the bipolar transistor comprises an npn transistor; and
    a measurement circuit coupled to the bipolar transistor and configured receive the amplified current;
    a first electrode; and
    a second electrode, wherein the current is responsive to a current flowing between the first electrode and the second electrode, wherein a base of the npn transistor is electrically coupled to the second electrode, and wherein a base-to-emitter voltage ($V_{BE}$) of the npn transistor is configured to bias the second electrode.

17. The apparatus of claim 16, further comprising another bipolar transistor electrically coupled with the npn transistor and configured to increase overall current amplification of the current.

18. The apparatus of claim 17, wherein an emitter of the npn transistor is coupled to a base of the other bipolar transistor and wherein a collector of the npn transistor is coupled to a collector of the other bipolar transistor.

19. The apparatus of claim 18, wherein the collector of the npn transistor and the collector of the other bipolar transistor are electrically coupled to a power supply voltage.

20. The apparatus of claim 16, further comprising a switch electrically coupled to an emitter of the npn transistor and configured to select an emitter current of the npn transistor to indicate the parameter.

21. A method for sensing, comprising:
supplying, by a sensor, a base current to a base of a bipolar transistor, wherein the supplying comprises generating the base current responsive to current flowing through a medium;
receiving the base current at the base of the bipolar transistor, the base current being indicative of a parameter;
amplifying the base current using the bipolar transistor to generate an amplified current;
determining the parameter based on the amplified base current;
causing the base current to flow through the medium between a first electrode and a second electrode; and
biasing the first electrode with a bias voltage.

22. An apparatus for sensing, comprising:
a sensor configured to supply a current indicative of a parameter;
a bipolar transistor having a base coupled to the sensor to receive the current, the bipolar transistor being configured to generate an amplified current based on the current, wherein the bipolar transistor comprises a pnp transistor; and
a measurement circuit coupled to the bipolar transistor and configured receive the amplified current.

23. The apparatus of claim 22, wherein the sensor is configured to supply the current responsive to one or more photons.

24. The apparatus of claim 22, wherein the sensor is configured to supply the current responsive to a current flowing through a medium.

25. The apparatus of claim 24, wherein the current flowing through the medium comprises ionic current.

26. The apparatus of claim 24, wherein the sensor is configured to supply the current responsive to a pH of the medium and wherein the parameter comprises the pH of the medium.

27. The apparatus of claim 24, wherein the medium comprises a solution with at least one deoxyribonucleic acid (DNA) fragment and wherein the parameter comprises a type of nucleobase in the DNA fragment.

28. The apparatus of claim 24, wherein the medium comprises an electrolytic solution and wherein the sensor is configured to supply the current based on molecules in the electrolytic solution.

29. The apparatus of claim 22, wherein the measurement circuit is configured to measure the amplified current.

30. The apparatus of claim 29, further comprising a processing system configured to determine the parameter based on the measured amplified current.

31. The apparatus of claim 22, further comprising a first electrode, wherein the sensor comprises:
a second electrode, wherein a base of the bipolar transistor is electrically coupled to the second electrode and wherein the current is responsive to a current flowing between the first electrode and the second electrode.

32. The apparatus of claim 22, further comprising a switch electrically coupled to a collector of the bipolar transistor and configured to selectively connect a collector current of the bipolar transistor to indicate the parameter.

33. The apparatus of claim 22, further comprising a first electrode, wherein the sensor comprises:
a second electrode, wherein the current is responsive to a current flowing between the first electrode and the second electrode, wherein a base of the pnp transistor is electrically coupled to the second electrode, and wherein an emitter-to-base voltage ($V_{EB}$) of the pnp transistor is configured to bias the second electrode.

34. The apparatus of claim 22, further comprising another bipolar transistor electrically coupled with the pnp transistor and configured to increase overall current amplification of the current.

35. The apparatus of claim 34, wherein an emitter of the pnp transistor is coupled to a base of the other bipolar transistor and wherein a collector of the pnp transistor is coupled to a collector of the other bipolar transistor.

36. The apparatus of claim 35, wherein the collector of the pnp transistor and the collector of the other bipolar transistor are electrically coupled to a reference potential.

37. The apparatus of claim 34, wherein a collector of the pnp transistor is coupled to a base of the other bipolar transistor and wherein the other bipolar transistor comprises an npn transistor.

38. The apparatus of claim 22, further comprising a switch electrically coupled to a collector of the pnp transistor and configured to selectively connect a collector current of the pnp transistor to indicate the parameter.

39. The apparatus of claim 22, further comprising:
a capacitor electrically coupled to a collector of the pnp transistor; and
a switch configured to discharge the capacitor to a reference potential during a first period and to allow a collector current of the pnp transistor to charge the capacitor during a second period.

40. An apparatus for sensing, comprising:
a sensor configured to supply a current indicative of a parameter;
a bipolar transistor having a base coupled to the sensor to receive the current, the bipolar transistor being configured to generate an amplified current based on the current, wherein the bipolar transistor comprises an npn transistor;
a measurement circuit coupled to the bipolar transistor and configured receive the amplified current; and
another bipolar transistor electrically coupled with the npn transistor and configured to increase overall current amplification of the current, wherein a collector of the npn transistor is coupled to a base of the other bipolar transistor and wherein the other bipolar transistor comprises a pnp transistor.

41. An apparatus for sensing, comprising:
a sensor configured to supply a current indicative of a parameter;
a bipolar transistor having a base coupled to the sensor to receive the current, the bipolar transistor being configured to generate an amplified current based on the current, wherein the bipolar transistor comprises an npn transistor;
a measurement circuit coupled to the bipolar transistor and configured receive the amplified current;
a capacitor electrically coupled to a collector of the npn transistor; and
a switch configured to charge the capacitor to a voltage level during a first period and to allow a collector current of the npn transistor to discharge the capacitor during a second period.

42. An apparatus for sensing, comprising:
- a sensor configured to supply a current indicative of a parameter;
- a bipolar transistor having a base coupled to the sensor to receive the current, the bipolar transistor being configured to generate an amplified current based on the current;
- a measurement circuit coupled to the bipolar transistor and configured receive the amplified current; and
- a resistive element electrically coupled to the bipolar transistor, wherein the resistive element is configured to convert the amplified current to a sensing voltage.

43. The apparatus of claim 42, further comprising a source follower configured to buffer the sensing voltage.

44. A device comprising:
- a plurality of measurement cells, each measurement cell comprising:
  - a sensor configured to supply a current indicative of a parameter; and
  - a bipolar transistor having a base coupled to the sensor to receive the current, the bipolar transistor being configured to generate an amplified current based on the current,
  wherein the bipolar transistor comprises a pnp transistor; and
- a plurality of analog-to-digital converters, wherein the bipolar transistor from the plurality of measurement cells is selectively coupled to one analog-to-digital converter of the plurality of analog-to-digital converters.

45. The device of claim 44, further comprising:
- a processing system configured to determine the parameter based on an output of the analog-to-digital converter.

46. The device of claim 44, further comprising a multiplexer configured to select one of the plurality of measurement cells and electrically couple the bipolar transistor of the measurement cell selected by the multiplexer to the analog-to-digital converter.

47. The device of claim 46, further comprising a first electrode, wherein the sensor comprises:
- a second electrode, wherein a base of the bipolar transistor is electrically coupled to the second electrode and wherein the current is in response to a current flowing between the first electrode and the second electrode.

48. The device of claim 47, wherein the first electrode is a common electrode for the plurality of measurement cells.

* * * * *